United States Patent
Sklar et al.

(10) Patent No.: US 11,471,231 B2
(45) Date of Patent: Oct. 18, 2022

(54) THERAPEUTIC GARMENT FOR TREATMENT OF OVER-SHUNTING HEADACHES AND METHOD FOR USE OF SAME

(71) Applicants: Frederick H. Sklar, Dallas, TX (US); Christina Marie Harrington, Prosper, TX (US)

(72) Inventors: Frederick H. Sklar, Dallas, TX (US); Christina Marie Harrington, Prosper, TX (US)

(73) Assignee: Frederick H. Sklar, Dallas, TX (US)

( * ) Notice: Subject to any disclaimer, the term of this patent is extended or adjusted under 35 U.S.C. 154(b) by 0 days.

(21) Appl. No.: 17/406,753

(22) Filed: Aug. 19, 2021

(65) Prior Publication Data

US 2022/0096186 A1    Mar. 31, 2022

Related U.S. Application Data

(63) Continuation-in-part of application No. 16/996,587, filed on Aug. 18, 2020, which is a continuation of
(Continued)

(51) Int. Cl.
*A61B 34/00* (2016.01)
*A61F 5/02* (2006.01)
*A61F 5/03* (2006.01)

(52) U.S. Cl.
CPC ........... *A61B 34/70* (2016.02); *A61F 5/02* (2013.01); *A61F 5/03* (2013.01)

(58) Field of Classification Search
CPC .......... A61F 5/028; A61F 13/148; A61F 5/02; A61F 5/03; A61F 5/34; A41D 2400/38; A61B 34/70
See application file for complete search history.

(56) References Cited

U.S. PATENT DOCUMENTS

| 5,205,815 A | 4/1993 | Saunders |
| 5,806,512 A * | 9/1998 | Abramov ............ A61M 16/202 601/150 |

(Continued)

FOREIGN PATENT DOCUMENTS

EP    2316521    5/2011

OTHER PUBLICATIONS

Sklar FH, Nagy L, Robertson BD, The Use of Abdominal Binders to Treat Over-Shunting Headaches, J Neurosurg Pediatr, Jun. 2012;9(6):615-620, doi: 10.3171/2012.2.PEDS11146, Children's Medical Center, Dallas, Texas, USA.
(Continued)

*Primary Examiner* — Thomas McEvoy
(74) *Attorney, Agent, or Firm* — Scott Griggs; Griggs Bergen LLP

(57) ABSTRACT

A therapeutic garment for treatment of over-shunting headaches and method for use of the same are disclosed. In one embodiment, the therapeutic garment includes a waistband and an abdominal portion that extends from the waistband to encircle the abdomen and hips from the groin to the costal margin of a person wearing the therapeutic garment. A binder portion is partially coincident to the abdominal portion. The binder portion includes a pressure subassembly including a network of interconnected channels having an inflation valve accessible from an exterior of the abdominal portion. The pressure assembly, when selectively inflated, provides a qualified degree of compression to distend an epidural venous plexus of the person wearing the therapeutic garment. The therapeutic garment may further be fashioned into a brief, a tank top, or include leg extensions.

6 Claims, 4 Drawing Sheets

Related U.S. Application Data application No. 13/767,651, filed on Feb. 14, 2013, now Pat. No. 10,743,954.

(60) Provisional application No. 63/067,868, filed on Aug. 19, 2020, provisional application No. 61/598,707, filed on Feb. 14, 2012.

(56) References Cited

U.S. PATENT DOCUMENTS

| | | |
|---|---|---|
| 6,463,765 B2 | 10/2002 | Blakely |
| 7,024,892 B2 | 4/2006 | Blakely |
| 8,257,289 B2 | 9/2012 | Vess |
| 8,568,195 B1 | 10/2013 | Schindler |
| 2009/0138064 A1 | 5/2009 | Horn |
| 2009/0192432 A1 | 7/2009 | Frazer |
| 2011/0054373 A1 | 3/2011 | Reiley |
| 2013/0095730 A1 | 4/2013 | Jensen |

OTHER PUBLICATIONS

International Searching Authority, International Search Report, PCT/US 13/26207, dated May 3, 2013.

* cited by examiner

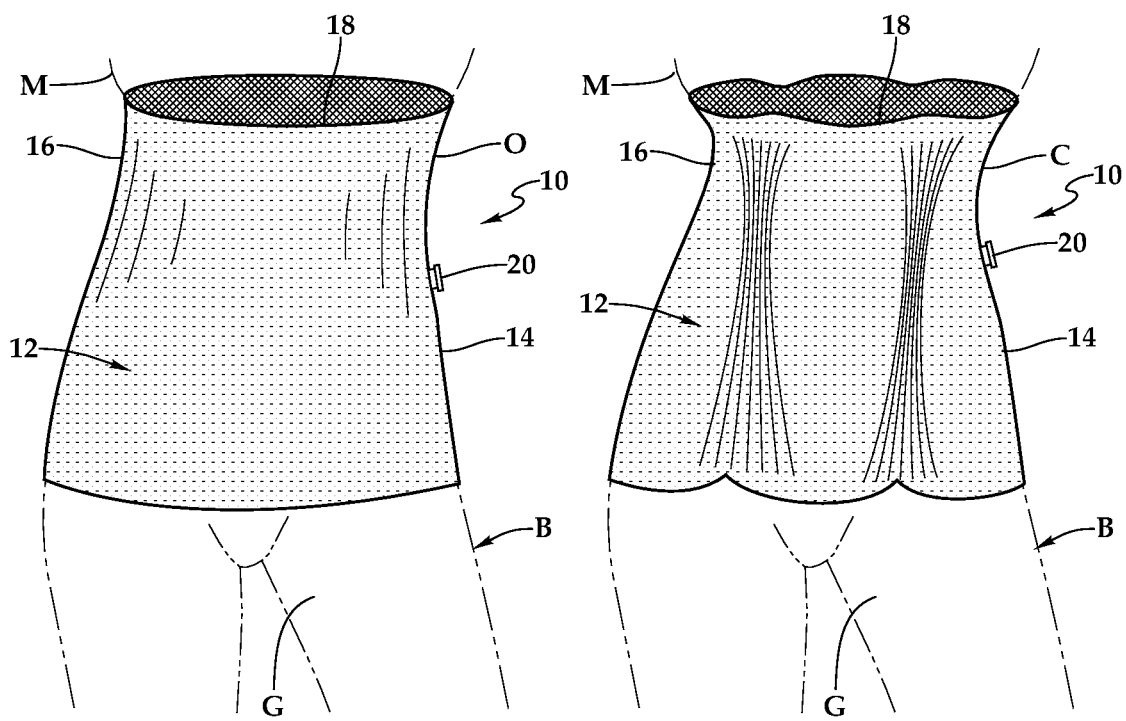
*Fig.1A*    *Fig.1B*
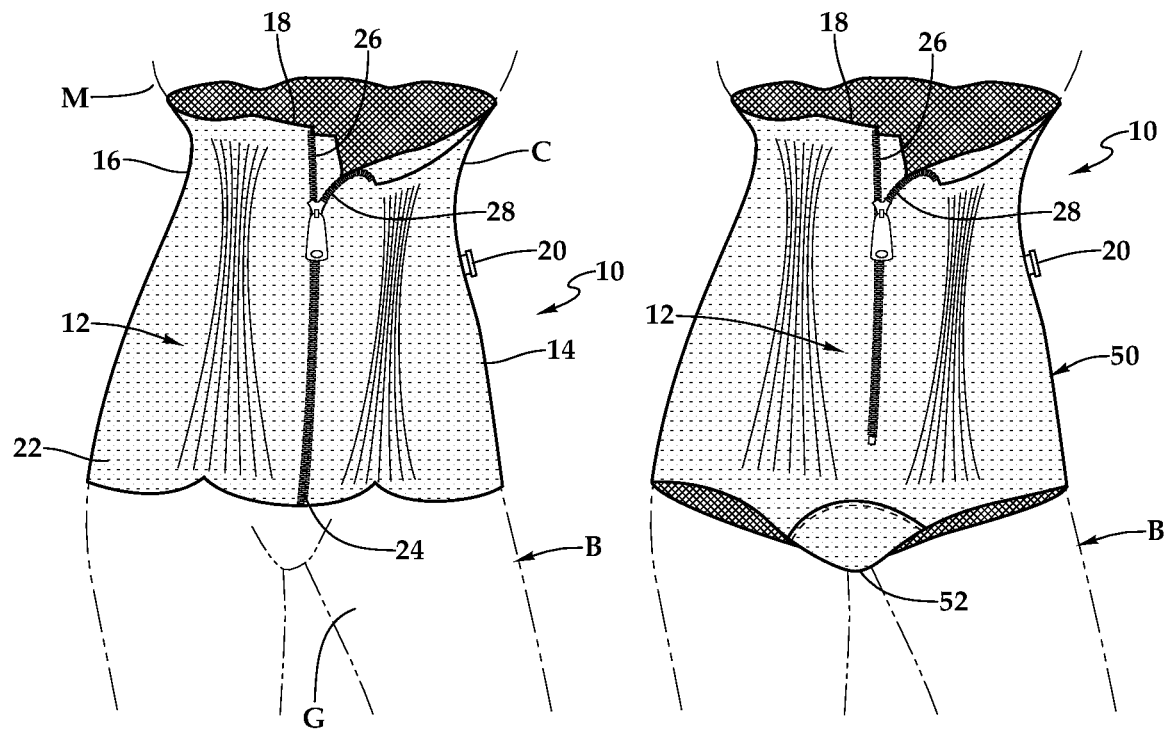
*Fig.2*    *Fig.3*

THERAPEUTIC GARMENT FOR TREATMENT OF OVER-SHUNTING HEADACHES AND METHOD FOR USE OF SAME

PRIORITY STATEMENT & CROSS-REFERENCE TO RELATED APPLICATIONS

This application claims priority from U.S. Patent Application No. 63/067,868, entitled "Therapeutic Garment for Treatment of Over-Shunting Headaches and Method for Use of Same" and filed on Aug. 19, 2020, in the name of Frederick H. Sklar; this application is a continuation-in-part of U.S. patent application Ser. No. 16/996,587, entitled "Therapeutic Garment for Treatment of Over-Shunting Headaches and Method for Use of Same" and filed on Aug. 18, 2020 in the name of Frederick H. Sklar; which is a continuation of U.S. patent application Ser. No. 13/767,651, entitled "Therapeutic Garment for Treatment of Over-Shunting Headaches and Method for Use of Same" and filed on Feb. 14, 2013, in the name of Frederick H. Sklar; now U.S. Pat. No. 10,743,954, issued on Aug. 18, 2020; which claims priority from U.S. Patent Application No. 61/598,707, entitled "Garments for Treatment of Over-shunting Headaches and Method for Use of Same," and filed on Feb. 14, 2012 in the name of Fredrick H. Sklar; which are hereby incorporated by reference, in entirety, for all purposes.

TECHNICAL FIELD OF THE INVENTION

This invention relates, in general, to the field of medical devices and, in particular, a therapeutic garment, and a method for use of same, for the treatment of over-shunting headaches in certain neurosurgical patients who are symptomatic of over-shunting and other neurosurgical conditions that cause intracranial hypotension.

BACKGROUND OF THE INVENTION

In adult and pediatric neurosurgery, cerebrospinal fluid (CSF) shunts are commonly used to treat hydrocephalus, arachnoid cysts, benign intracranial hypertension (pseudotumor cerebri), and other neurosurgical conditions characterized by raised intracranial pressure (ICP). Shunt over-drainage of CSF occurs with frequency—some shunts more than others. These patients develop intracranial hypotension, presumably related to the siphoning of CSF from the head when the patient is upright. This condition is referred to as over-shunting.

Children and adults with over-shunting frequently experience headaches. In a recent retrospective clinical review, 23% of shunted patients had headaches that were thought by the neurosurgeon to be the result of over-shunting on the basis of their clinical pictures. In addition, there are patients with headaches resulting from intracranial hypotension, due to the escape or over-drainage of CSF as a result of a lumbar puncture (the so-called spinal tap headache), post-operative pseudomeningocele, and chronic CSF leakage (CSF ottorhea and rhinorrhea).

Over-shunting headaches are usually intermittent. They tend to come on later in the day; patients rarely awaken with headache. There is frequently a postural component: laying down helps the headache. The ventricles are usually small on MRI or CT scan. Intracranial pressure is low, as indicated by introducing a needle into the shunt (the so-called shunt tap). A need exists for a solution to over-shunting headaches in particular patients.

SUMMARY OF THE INVENTION

It would be advantageous to achieve garments for treatment of over-shunting headaches and a method for use of the same. It would also be desirable to enable a physiological-medical based solution that would be non-encumbering and allow patients to use the solution while going about a daily routine. To better address one or more of these concerns, in one aspect of the invention, therapeutic garments for treatment of over-shunting headaches and a method for use of the same are disclosed. In one embodiment, the therapeutic garment includes a waistband and an abdominal portion that extends from the waistband to encircle the abdomen and hips from the groin to the costal margin of a person wearing the therapeutic garment.

A binder portion is partially coincident to the abdominal portion. The binder portion includes a pressure subassembly including a network of interconnected channels having an inflation valve accessible form an exterior of the abdominal portion. The pressure assembly, when selectively inflated, provides a qualified degree of compression to distend an epidural venous plexus of the person wearing the therapeutic garment. The therapeutic garment may further be fashioned into a brief, a tank top, or include leg extensions.

In another embodiment, a method for treating over-shunting headaches is provided. The method includes using a ventriculostomy for monitoring intracranial pressure and pulsations in a shunted patient experiencing over-shunting headaches and then providing a therapeutic garment for the patient experiencing headaches to rule out the diagnosis of a poorly functioning shunt. If the pressure is not found to be elevated, but rather low with abnormally increased pulsations, the patient likely has symptomatic over-shunting and can be provided a therapeutic garment. To wear while intracranial pressure (ICP) is being monitored. The therapeutic garment may be tailored for the patient. The methodology includes selectively inflating the pressure subassembly to provide a qualified degree of compression to distend an epidural venous plexus of the person wearing the therapeutic garment in order to see if this reduces the abnormally increased intracranial pulsations. The effect of wearing the garment on intracranial pulsations may be predictive whether continued wearing of the therapeutic garment for a specified time will effectively treat the patient's over-shunting headaches.

In patients, the therapeutic garment presented herein fulfills a need that exists in patients suffering from over-shunting headaches. Patients wearing the therapeutic garment on the abdomen twenty four (24) hours a day for four to six (4-6) weeks have fewer headaches. Approximately 87% of patients experience marked improvement or complete relief of over-shunting headaches with the use of the therapeutic garment. Moreover, 71% of patients who have a favorable response to the use of the therapeutic garment experience complete relief of headache. Further, the headache relief usually persists after the therapeutic garment is removed. The majority of patients (59%) start having headache again, but usually after a year or more. Recurrent headache responds to reuse of the therapeutic binder in 79% of patients. These and other aspects of the invention will be apparent from and elucidated with reference to the embodiments described hereinafter.

BRIEF DESCRIPTION OF THE DRAWINGS

For a more complete understanding of the features and advantages of the present invention, reference is now made to the detailed description of the invention along with the accompanying figures in which corresponding numerals in the different figures refer to corresponding parts and in which:

FIG. 1A is a front schematic diagram of one embodiment of a therapeutic garment for treatment of over-shunting headaches in a closed position being worn by a person, according to the teachings presented herein;

FIG. 1B is a front schematic diagram of the therapeutic garment of FIG. 1A in a closed position being worn by the person;

FIG. 2 is a front perspective diagram of another embodiment of a therapeutic garment, according to the teachings presented herein;

FIG. 3 is a front perspective diagram of another embodiment, labeled a brief embodiment, of a therapeutic garment for treatment of over-shunting headaches;

DETAILED DESCRIPTION OF THE INVENTION

Figure 4:
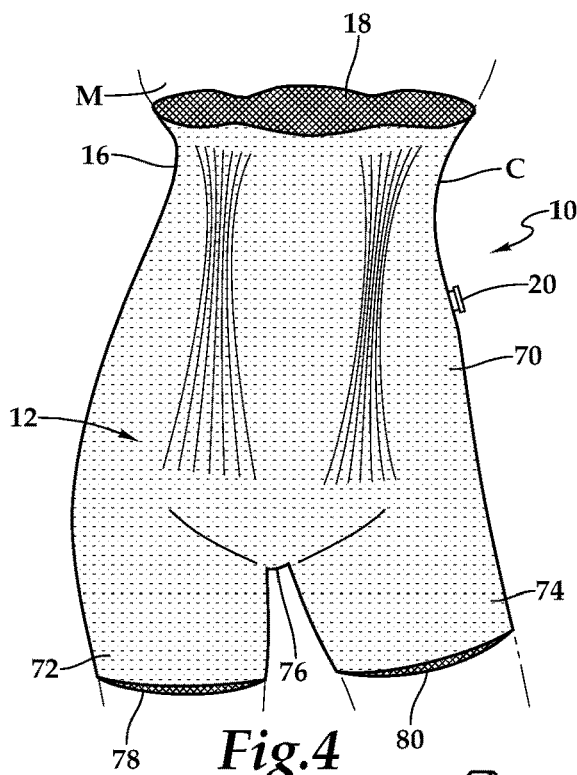
FIG. 4 is a front perspective diagram of a further embodiment, a leg extension embodiment, of a therapeutic garment for treatment of over-shunting headaches.

While the making and using of various embodiments of the present invention are discussed in detail below, it should be appreciated that the present invention provides many applicable inventive concepts, which can be embodied in a wide variety of specific contexts. The specific embodiments discussed herein are merely illustrative of specific ways to make and use the invention, and do not delimit the scope of the present invention.

Referring initially to FIGS. 1A and 1B, therein is depicted a therapeutic garment for treatment of over-shunting headaches that is schematically illustrated and generally designated 10, being worn in FIGS. 1A and 1B by a person B. The therapeutic garment 10 includes a pressure subassembly 12 as well as a waistband 14 and an abdominal portion 16 that extends from the waistband 14 to encircle the abdomen and hips from the groin G to the costal margin M of the person B wearing the therapeutic garment 10. A binder portion 18 is partially coincident to the abdominal portion 16. In one embodiment, the abdominal portion 16 and binder portion 18 are integral and integrally formed and thereby define an interior for contact with the person and an exterior. The abdominal portion 16 and binder portion 18 may be formed of an elastic, latex-free material. Alternatively, Lycra yarn, spandex yarn, nylon yarn, or a plane-knit based fabric may be utilized. An inflation valve 20 is coupled to the pressure subassembly 12 and is accessible from an exterior of the abdominal portion 16.

As shown, the binder portion 18 has open and closed positions, which are labeled as open position O and closed position C. The binder portion 18 in the closed position 22 is configured to distend the epidural venous plexus of the person 12 wearing the therapeutic garment. The pressure assembly 12, when selectively inflated via the inflation valve 20, provides a qualified degree of compression to distend an epidural venous plexus of the person B wearing the therapeutic garment 10. When selectively inflated, the therapeutic garment 10 is in the closed position C and is difficult to remove. On the other hand, when selectively deflated, the therapeutic garment 10 is in the open position O and may more easily be removed from the person B. Referring now to FIG. 2, a closure mechanism 24 may also be included in the therapeutic garment 10. The close mechanism 24 may be a zipper, Velcro fastener, or other closing mechanism. The closure site may be backed by a narrow flap of soft, non-elastic material for patient comfort.

As illustrated, a vertical opening 26 with a flap 28 may extend along the garment axially to provide a location for the closure mechanism 24. As an alternative or addition, drawcord pulley laces may be included to further facilitate application of the therapeutic garment 10. Such an alternative or addition may be particularly useful with obese teenagers or adults with a pendulous abdomen. Further, although not shown, a print or design may be added to the therapeutic garment 10.

Referring now to FIGS. 1A, 1B, and 2, in these embodiments, the neurosurgical abdominal binders or therapeutic garments may be tailored into a gentle hour-glass shape to facilitate a good fit at the waist. The therapeutic garments are manufactured in multiple sizes to extend from the patient's costal margins down to the groin. Thus, the vertical height of the therapeutic garment is an important determination of size, ranging from 8" to 16" inches (approximately 20 to 40 centimeters), and can be made available at various intermediate increments. This system will allow appropriate sizing of patients, ranging from small infants to tall adults. Multiple tubular circumferences based on body habitus will be available for each vertical height measurement. In addition, longer circumferential length binders are also available to accommodate full sized adult patients.

Figure 5:
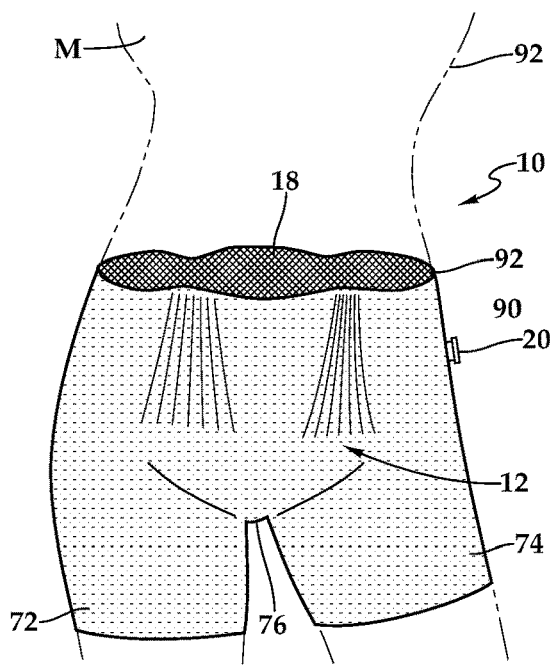
FIG. 5 is a front perspective diagram of a still further embodiment, a leg extension with reduced height embodiment, of a therapeutic garment for treatment of over-shunting headaches.

Referring to FIG. 3, one embodiment of the therapeutic garment 10 for treatment of over-shunting headaches is depicted, wherein the therapeutic garment 10 is incorporated into a brief 50 having a crotch 52, which may include appropriate access openings. Referring to FIG. 4, another embodiment of the therapeutic garment 10 is shown, a leg extension embodiment 70. Leg portions 72, 74 extend down from the abdominal portion to define a crotch portion 76 therebetween. Leg binder portions 78, 80 are coincident with the leg portions 72, 74. The leg binder portions 78, 80 are configured to exert pressure on the supra-pubic and inguinal ligament groin areas of the person wearing the therapeutic garment. FIG. 5 depicts a further variation wherein a leg extension embodiment 90 includes a reduced height 92. The abdominal portion extends from the waistband to encircle the abdomen and hips from the groin to an anterior costal margin location of a person wearing the therapeutic garment. With respect to the leg extensions, extension of the elastic fabric of the brief down onto the thighs may be desirable for additional compression of the femoral veins at the inguinal ligaments. This may improve binder function in cases of persistent headache despite the use of the standard neurosurgical binder or binders with briefs. Girls and women may prefer this option for fashion considerations.

Figure 6:
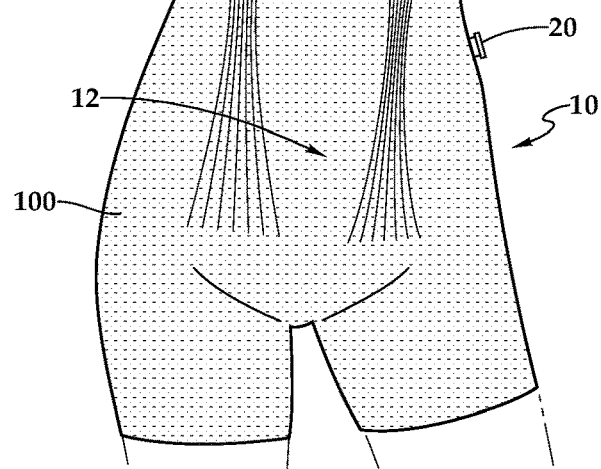
FIG. 6 is a front perspective diagram of an additional embodiment, a tank top embodiment, of a therapeutic garment for treatment of over-shunting headaches.

FIG. 6 is a still further embodiment of the therapeutic garment, wherein the therapeutic garment is incorporated into a tank top 100 having shoulder straps 102, 104. This embodiment will allow maximal physical activity without dislodging binder placement. The patient or person would step into the therapeutic garment at the neck opening and pull the top of the elastic component up to the costal margins. The shoulder straps 102, 104 are then slipped into place. Fabric above the costal margin and that of the shoulder straps do not have to be elastic.

Figure 7A:
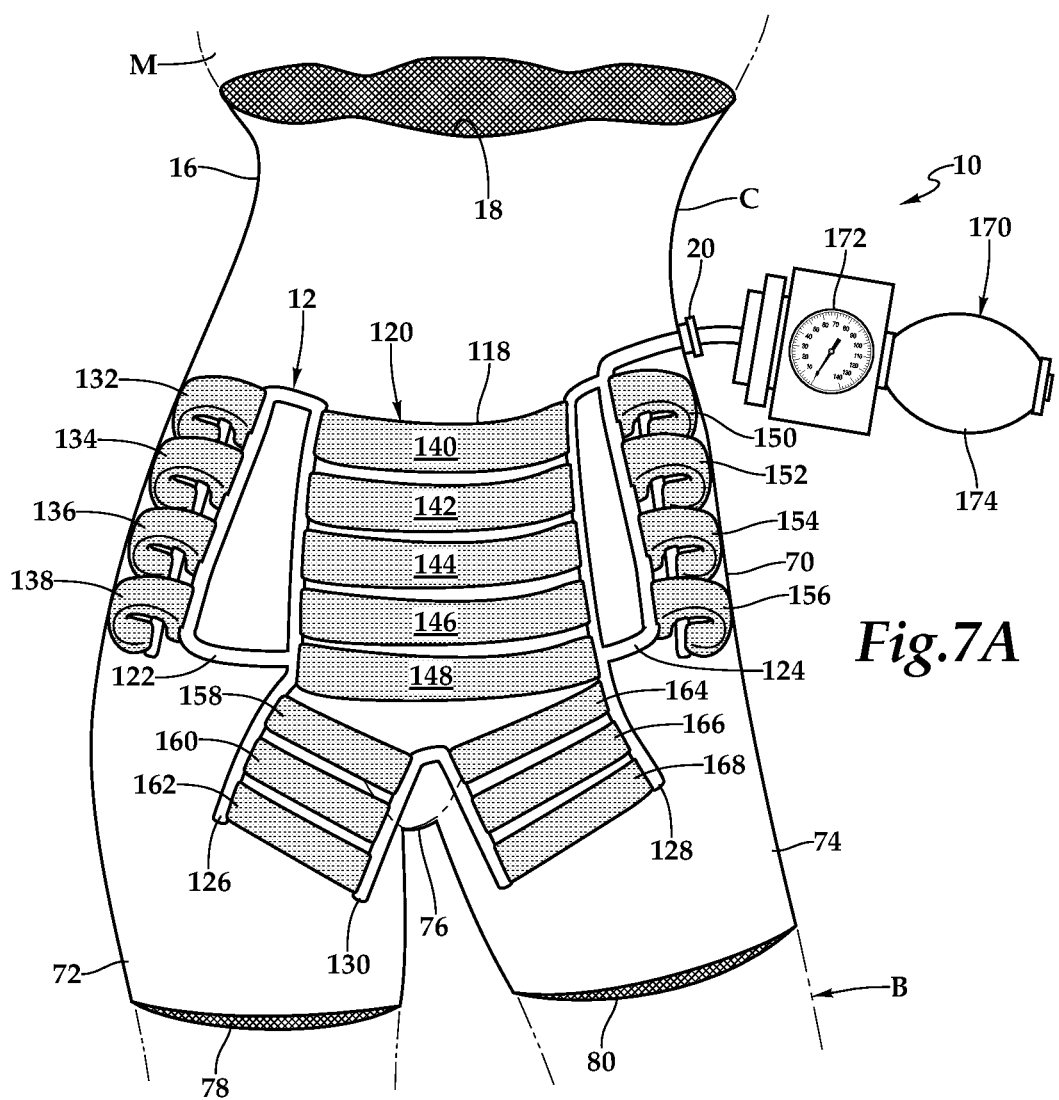
FIG. 7A is a front perspective, in partial cross-section, of one embodiment of a pressure subassembly of the therapeutic garment depicted in FIG. 4.
Figure 7B:
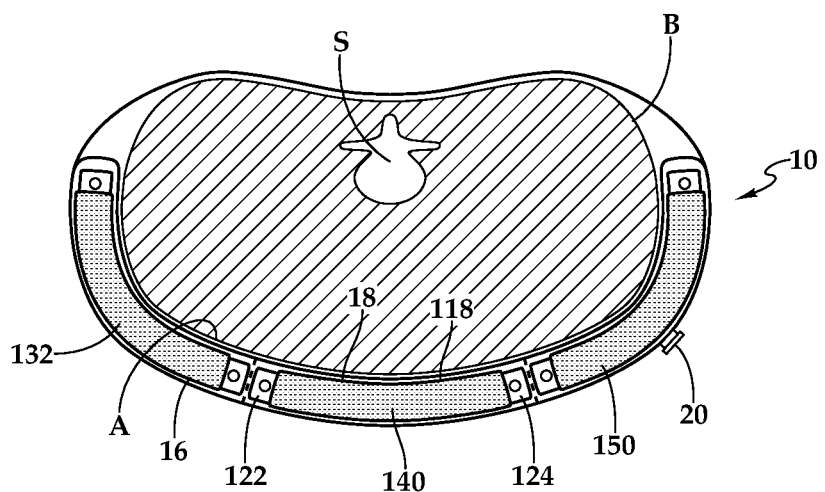
FIG. 7B is a top plan view, in cross-section, of the pressure assembly and therapeutic garment depicted in FIG. 7A.

Referring now to FIGS. 7A and 7B, with respect to therapeutic garment 10, one embodiment of the pressure subassembly 12 is housed within a pocket 118 of the binder portion 18. As shown, the pocket 118 and the binder portion 18 are partially coincident to the abdominal portion 16 at an anterior abdominal wall A, extending laterally between each posterior axillary line. Vertically, the pocket 118 and the binder portion 18 may extend from the costal margin down onto the thighs so as to provide compression of the groin region. For reference, the spine of the person B is also depicted. The pressure subassembly 12 includes a network of interconnected channels 120 that are coupled and placed in communication with the inflation valve 20. Within the network of interconnected channels 120, connection matrix portions 122, 124, 126, 128, 130 support flattened silicone tubing 132, 134, 136, 138, 140, 142, 144, 146, 148, 150, 152, 154, 156, 158, 160, 162, 164, 166, 168. The flattened silicone tubing 132-168 may be portions of 1" (2.54 cm) diameter Penrose drain, in one embodiment, with adequate elastic strength. The inner fabric of the pocket 118 may be quilted to the outer fabric of the therapeutic garment 10, with stitching between the various flattened silicone tubing 132-168. Such an arrangement would mitigate against migration and would further even distribution of the pressure in the desired area.

A diagnosis of symptomatic intracranial hypotension requires the physician to understand why the intracranial pressure is low. Most of the time, over-shunting is the reason for the intracranial hypotension. Lumbar puncture headaches and postoperative pseudomeningoceles account for most of the remaining patients. In shunted patients, most have only headaches. If the symptoms are severe, such as altered level of consciousness, vomiting, cranial nerve dysfunction, consideration should be given to surgery. Adding an anti-siphon device to the shunt sometimes is effective; cranial morcellation procedures in children and teenagers is frequently effective. In some patients, it is difficult to distinguish between the patient's having a poorly functioning ventricular shunt from a shunt that is working too well (over-shunting).

The patients require a good examination, including a funduscopic examination that rules out papilledema, which may occur with high pressure and a failed shunt. Usually, CT and MRI scans are the first diagnostic steps to evaluate these sick patients, but on occasion the diagnostic distinction between over-shunting and a failed shunt is not obvious from these studies. Shunt taps should be done, although the results may also be indecisive. In these patients, ICP monitoring may be an important part of the clinical evaluation. Some patients with over-shunting have very low ICP as a baseline, superimposed with intermittent episodes of extremely high pressure plateau waves. The pressures can be noted to increase gradually from 1-2 mm Hg, which is very low, for example, to 80 mm Hg (which is very high) lasting 10-20 minutes, for instance, and then suddenly return to the low baseline. These plateau waves are thought to reflect a hyper-reactive vascular bed, perhaps related to the very large intracranial pulse pressure (PP). This is mentioned because performing a shunt tap during one of these plateau waves, the physician may interpret the pressure of 80 mm Hg to indicate that the problem is a "blocked shunt" and rush the patient to the OR for an emergency shunt revision, which will not remedy the patient's over-shunting. On the other hand, most patients with intracranial hypotension are not horribly sick. They may be very uncomfortable with the headache, but otherwise, the symptoms tend not to be severe. These are the patients that should have a trial of wearing a neurosurgical compression garment once their neurosurgical assessment has ruled out shunt failure.

With traditional post-surgical abdominal binders, the patient's wearing the binder for 4-6 weeks, 24 hours a day, will make the headache go away 87% of the time. It is suggested that this is a very high success rate! Typically, the headache starts improving after only several days of wearing the binder. Some children have said they felt better the very first day they had a binder. In a small group of other patients who ultimately get relief of headache with a binder, it can take a week or two before the headache goes away. With an active pressure-controlled neurosurgical binder, these latter patients should surely have had their physician increase the compression pressure, were the device available at that time.

The passive neurosurgical binders that have associated briefs—into which the patient must step and pull up into place—allow the patients to be active in sports and other exercise activities without having to deal with the "riding up" of the binder above the groin area. Indeed, the groin area may be the most effective area of compression in treating this condition. Neurosurgical garments that look like clothes will be more acceptable to patients of all ages, especially the children. The neurosurgical garments can have colorful and graphic design features that will encourage young patients to wear them.

Further, an active pressure-control garment, like the therapeutic garment 10 presented herein, provides broad opportunities to construct the most effective neurosurgical garment possible and to use this device to do meaningful medical research that may clarify the mechanism of action of the binder, as well as the pathophysiology of over-shunting and symptomatic intracranial hypotension. If the various inflatable channels are not all on the same pressure circuit, but rather arranged for regional control, various compression sites can be studied effectively not only in patients as a group, but in a particular patient—perhaps one who is not having a good response. One concern is that pressure over the groin area may result in lower extremity venous stasis, ankle swelling, and perhaps even venous thrombosis. This therefore requires close physician follow-up as well as educating the patient to be aware of leg swelling, for instance, so that the doctor can be notified. Moreover, if compression of the groin area is indeed the most effective site to achieve relief of symptoms (or reduction of intracranial PP if it were to be measured), perhaps the attending physician can have the patient apply a pressure of 30 mm Hg to the right groin and 15 mm Hg to the left on odd days, and the reverse, on even days. An alternative regiment would be half days. These specific timing maneuvers may avoid venous stasis complications entirely. Alternatively, high and low pressures between the upper abdominal grids as one group and the groin grids as the other can be selectively carried out under physician control. Other combinations are also possible. All require close physician monitoring, at least until the doctors gain some experience with this treatment.

As shown, a pressure gauge and pump combination 170, which includes a pressure gauge 172 and a pump 174, is provided to mate with the inflation valve 20 and selectively inflate the therapeutic garment 10. The pressure gauge and pump combination 170 may include electronic, digital, analog, and manual components. The pressure gauge and pump combination 170 provide a qualified degree of compression to distend the appropriate portion of the person B, such as the epidural venous plexus of the person B wearing the therapeutic garment 10. By way of example, the qualified degree of compression may be between about 10 mm Hg and about 30 mm Hg. By way of another example, the qualified degree of compression may be about 20 mm Hg. The therapeutic garment 10 therefore allows the clinician to prescribe a qualified degree of compression appropriate for the patient. The person B wearing the therapeutic garment 10 may inflate the therapeutic garment 10 to the appropriate compression after putting on the therapeutic garment 10. Further, the person B wearing the therapeutic garment may deflate the therapeutic garment 10 prior to removing the therapeutic garment 10.

Figure 8A:
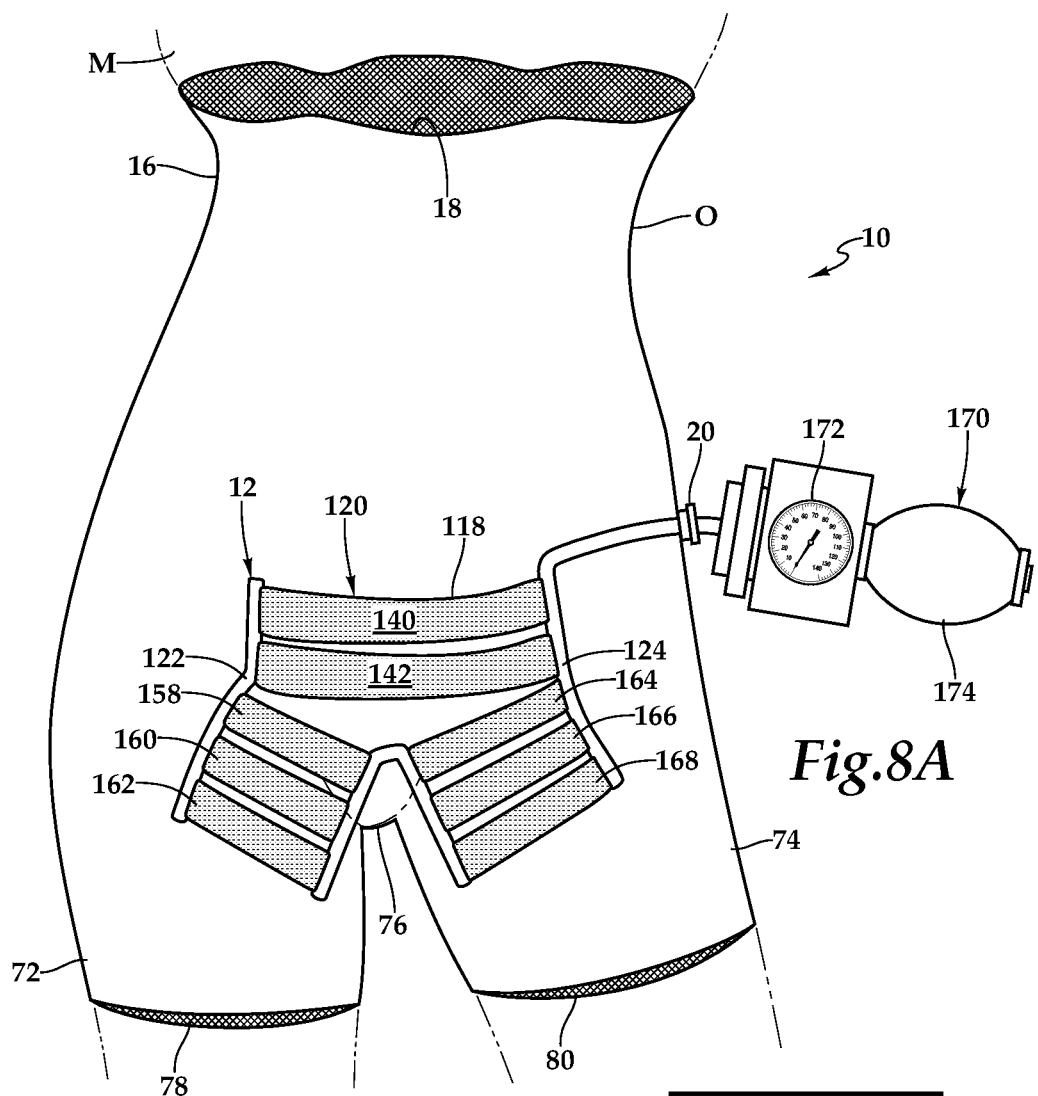
FIG. 8A is a front perspective, in partial cross-section, of another embodiment of a pressure subassembly of the therapeutic garment depicted in FIG. 4.
Figure 8B:
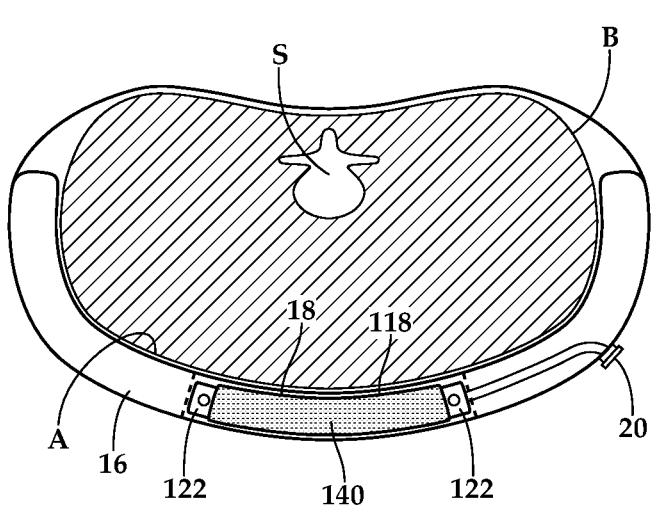
FIG. 8B is a top plan view, in cross-section, of the pressure assembly and therapeutic garment depicted in FIG. 8A.

It should be appreciated that the network of interconnected channels 120 may have various grid arrangements. By way of example and not by way of limitation, one grid arrangement has a central channel grouping that covers the mid to upper abdominal region and a lateral grid on each side of the abdominal grid. In use, this arrangement covers approximately two-thirds of an anterior perimeter of the torso at abdominal level. In addition, as shown in FIGS. 7A and 7B, each groin may be covered with a channel grid. Further, all of the flattened silicone tubing 132-168 may be oriented horizontally to allow the person B to bend at the waist and groins as well as change sitting positions. Referring now to FIGS. 8A and 8B, as compared to FIGS. 7A and 7B, an alternative grid arrangement is presented. It should be appreciated that in some individuals, localized pressure on the lower abdomen and groins may be sufficient in treating the symptoms of intracranial hypotension, other individuals may require that longer lengths of flattened silicone tubing be employed over a larger area.

Figure 9:
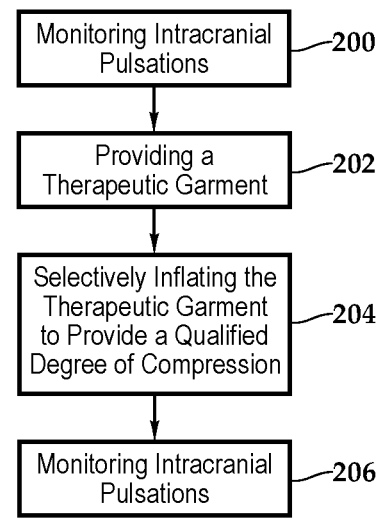
FIG. 9 is flow chart depicting one embodiment of a method for treatment of over-shunting headaches, according to the teachings presented herein.

Referring now to FIG. 9, one embodiment of a methodology for treating over-shunting headaches is provided. The methodology begins at block 200 wherein monitoring intracranial pressure and pulse pressure in a patient experiencing over-shunting headaches occurs. At block 202, a therapeutic garment, which may be specifically tailored, is provided for the patient experiencing over-shunting headaches. As previously discussed, the therapeutic garment may include a waistband and an abdominal portion that extends from the waistband to encircle the abdomen and hips from the groin to the costal margin of a person wearing the therapeutic garment. A binder portion, which includes a pressure subassembly, is partially coincident to the abdominal portion. As also previously discussed, the pressure subassembly may include a network of interconnected channels having an inflation valve accessible from an exterior of the abdominal portion. The methodology continues at block 204 where the pressure subassembly is selectively inflated to provide a qualified degree of compression to distend an epidural venous plexus of the person wearing the therapeutic garment. This thereby provides treatment of over-shunting headaches. In patients considered more symptomatic, in some embodiments, the methodology presented herein includes monitoring intracranial pressure and pulse pressure with shunts to distinguish shunt malfunction from over-shunting, after which those over-shunting patients with low ICP and increased PP may be placed in a therapeutic garment during monitoring to measure the effects of qualified degree of compression of at least one of groins and abdomen as a potential predictor of treatment efficacy. At block 206, the methodology continues with monitoring, while the patient wears the therapeutic garment, intracranial pressure and pulse pressure are measured in the patient experiencing over-shunting headaches.

As described herein, therapeutic garments have been developed that exert pressure on the abdomens and groins of children and adult patients with headaches related to over-shunting or other causes of intracranial hypotension. These garments act as neurosurgical abdominal binder and the described spectrum of therapeutic garments includes, but is not limited to a unisex abdominal binder, a binder having a pressure subassembly therein incorporated into a fitted, elastic brief, a binder-brief combination with over-the-shoulder support, and binder-briefs with leg extensions. In addition, the garments can be designed to be appealing for male or female usage, respectively; to be appealing to specific age groups; and to provide an effective fit over a spectrum of body shapes.

With respect to physiology, intracranial pulse pressures increase with the level of ICP. This is a feature of physiology. In hydrocephalus, this pulse pressure-ICP relationship is exaggerated and the intracranial pulse pressure is abnormally increased at the higher pressures. Using CSF withdrawals, it has been shown that reducing pressures below the physiologic baseline will result in marked augmentation of the intracranial pulse pressure—not unlike the pulse pressure increase that is seen at high pressures. Normally, the pressure pulsations of the arteries at the base of the brain displace the CSF of the basal cisterns down the clivus into the spine with each cardiac systole. This can be appreciated on gated CSF studies with an MRI technique. Studying patients undergoing myelography, it has been demonstrated that breathing 5% carbon dioxide causes the spinal sac to enlarge.

On the other hand, hyperventilation causes the brain volume to decrease, and the spinal sac gets smaller as CSF moves back into the head. The spinal epidural veins are in free communication with the large veins of the chest and abdomen, and these epidural veins likely get smaller or enlarge to accommodate CSF movement into and out of the spine during systole and diastole, respectively. In other words, the spinal epidural veins may serve as a shock absorber, since epidural blood can be displaced during systole into the great veins of the chest and abdomen with each bolus of CSF displaced from the head into the spine. In diastole, CSF flow changes direction and moves out of the spine back towards the Circle of Willis. This is a physiologic process.

However, with over-shunting, the volume of CSF is reduced, not only in the ventricles, but also in the cisterns at the base of the brain. It is suggested that the reduced volume of CSF in the basal cisterns cannot effectively transmit the arterial pressure pulsations into the spine where reciprocal pulsatile changes in epidural venous blood can dampen these arterial pulsations. The intracranial pulse pressures become augmented, and the patient may experience adverse symptoms (e.g., headache) or signs (VI nerve palsy). It is suggested that the therapeutic garment possibly functions to compress the pelvic veins, which are in free communication with the epidural venous plexus. It is hypothesized that the therapeutic garment distends the epidural venous plexus so that it can function better as a shock absorber; more venous blood can be transiently displaced out of the spine with each systole. The result is a reduction of intracranial pulsations and improvement in signs and symptoms.

The order of execution or performance of the methods and process flows illustrated and described herein is not essential, unless otherwise specified. That is, elements of the methods and process flows may be performed in any order, unless otherwise specified, and that the methods may include more or less elements than those disclosed herein. For example, it is contemplated that executing or performing a particular element before, contemporaneously with, or after another element are all possible sequences of execution.

While this invention has been described with reference to illustrative embodiments, this description is not intended to be construed in a limiting sense. Various modifications and combinations of the illustrative embodiments as well as other embodiments of the invention, will be apparent to persons skilled in the art upon reference to the description. It is, therefore, intended that the appended claims encompass any such modifications or embodiments.

What is claimed is:

1. A method for treating over-shunting headaches, the method comprising:
    monitoring intracranial pressure (ICP) and pulse pressure (PP) in a patient experiencing over-shunting headaches;
    providing a therapeutic garment for the patient experiencing over-shunting headaches from a plurality of therapeutic garments, each therapeutic garment including:
        a waistband;
        an abdominal portion that extends from the waistband to encircle the abdomen and hips from the groin to the costal margin of a person wearing the therapeutic garment;
        a binder portion partially coincident to the abdominal portion, the binder portion having a pressure subassembly therein; and
        the pressure subassembly including a network of interconnected channels having an inflation valve accessible from an exterior of the abdominal portion;
    electively inflating the pressure subassembly to provide a qualified degree of compression to distend an epidural venous plexus of the the patient thereby providing treatment of the over-shunting headaches; and
    monitoring intracranial pressure and pulse pressure in additional patients with shunts to distinguish shunt malfunction from over-shunting, after which placing those over-shunting patients with low ICP and increased PP in one of the therapeutic garments during the monitoring to measure the effects of applying the qualified degree of compression to at least one of the groin and abdomen as a potential predictor of treatment efficacy.

2. The method as recited in claim 1, wherein providing the therapeutic garment for the patient experiencing over-shunting headaches further comprises tailoring the therapeutic garment for the patient.

3. The method as recited in claim 1, wherein the qualified degree of compression applied to the patient is between about 10 mm Hg and about 30 mm Hg.

4. The method as recited in claim 1, wherein the qualified degree of compression applied to the patient is about 20 mm Hg.

5. The method as recited in claim 1, further comprising providing the qualified degree of compression to the patient via the inflation valve mated with a pressure gauge and pump combination.

6. The method as recited in claim 1, further comprising providing the qualified degree of compression to the patient via the inflation valve mated with an electronic pump.

* * * * *